(12) United States Patent
Froese

(10) Patent No.: US 9,775,804 B2
(45) Date of Patent: Oct. 3, 2017

(54) INTERNAL STRUCTURED SELF ASSEMBLING LIPOSOMES

(71) Applicant: Aaron Froese, Hamilton (CA)

(72) Inventor: Aaron Froese, Hamilton (CA)

(*) Notice: Subject to any disclaimer, the term of this patent is extended or adjusted under 35 U.S.C. 154(b) by 0 days.

(21) Appl. No.: 14/420,983

(22) PCT Filed: Aug. 14, 2013

(86) PCT No.: PCT/CA2013/050622
§ 371 (c)(1),
(2) Date: Feb. 11, 2015

(87) PCT Pub. No.: WO2014/026284
PCT Pub. Date: Feb. 20, 2014

(65) Prior Publication Data
US 2015/0231074 A1 Aug. 20, 2015

Related U.S. Application Data

(60) Provisional application No. 61/682,897, filed on Aug. 14, 2012.

(51) Int. Cl.
*A61K 9/127* (2006.01)
*A61K 47/26* (2006.01)

(52) U.S. Cl.
CPC .......... *A61K 9/1272* (2013.01); *A61K 9/1274* (2013.01); *A61K 9/1277* (2013.01); *A61K 47/26* (2013.01)

(58) Field of Classification Search
CPC .... A61K 47/26; A61K 9/1272; A61K 9/1274; A61K 9/1277; A61K 31/7105; A61K 31/713; A61K 9/127
USPC .............................................. 424/178.1, 450
See application file for complete search history.

(56) References Cited

U.S. PATENT DOCUMENTS 6,147,204 A * 11/2000 Gold .................... A61K 9/1271
424/450

FOREIGN PATENT DOCUMENTS

| CA | 2567741 | 3/2006 |
|---|---|---|
| CA | 2793604 | 9/2011 |
| WO | 92/21329 | 12/1992 |
| WO | 01/49265 | 7/2001 |

OTHER PUBLICATIONS

International Search Report and Written Opinion from corresponding PCT Appln. No. PCT/CA2013/050622.
Ng et al., "Properties of a self-assembled phospholipid membrane supported on lipobeads", Biophysical Journal, 87, Canada, 2004, pp. 323-331.
Buck et at., "Engineering lipobeads: Properties of the hydrogel core and the lipid bilayer shell", Biomacromolecules, Canada, 2004, 5, pp. 2230-2237.
Gutmayer et al., "Synthesis of a polymer skeleton at the inner leaflet of liposomal membranes: Polymerization of membrane-adsorbed pH-sensitive monomers", Biomacromolecules, Germany 2006, 7, pp. 1422-1428.
Stauch et al., "Mimicking a cytoskeleton by coupling Poly(N-isopropylacrylamide) to the inner leaflet of liposomal membranes: Effects of photopolymerization on vesicle shape and polymer architecture", Biomacromolecules, Germany 2002, 3, pp. 324-332.
Dayani et al., "Liposomes with double-stranded DNA anchoring the bilayer to a hydrogel core", Biomacromolecules, California, 2013, 14, pp. 3380-3385.
Office Action from related EPO Appln. No. 13829520.9 dated Apr. 12, 2016.
Saleem et al., "Lipogels: Single-Lipid_Bilayer-Enclosed Hyrdogel Spheres", Biomacromolecules, vol. 12, No. 6, Jun. 13, 2011, pp. 2364-2374, Ontario, Canada.

* cited by examiner

*Primary Examiner* — Janet Epps-Smith
(74) *Attorney, Agent, or Firm* — Grossman, Tucker, Perreault & Pfleger, PLLC

(57) ABSTRACT

The specification relates to an internal structured self assembled liposome (ISSAL), containing a nuclear core molecule or complex including a first affinity enhancing molecule; and a phospholipid-affinity enhancing complex having a phospholipid coupled to second affinity enhancing molecule, wherein the second affinity enhancing molecule couples to the first affinity enhancing molecule. The ISSAL's can be used in, for example and without limitation, the field of drug delivery, vaccination, imaging contrast agents, and nanotechnology, in which liposomes of ordered, self-assembling structure are employed to deliver soluble or insoluble molecules to any sub-cellular address.

18 Claims, 8 Drawing Sheets

100 nm
Direct Mag: 200000x

INTERNAL STRUCTURED SELF ASSEMBLING LIPOSOMES

CROSS-REFERENCE TO RELATED APPLICATIONS

This is the U.S. National Phase Application under 35 U.S.C. §371 of International Patent Application No. PCT/CA2013/050622 filed Aug. 14, 2013, which claims the benefit of U.S. Provisional Patent Application Ser. No. 61/682,897 filed Aug. 14, 2012, both of which are incorporated by reference herein.

FIELD

The present invention relates to internal structured self-assembled liposomes (ISSAL), their process for manufacture and uses or applications.

BACKGROUND

Drug Delivery Using Liposomes Over Conventional Delivery Methods

Drug delivery methods have become a hot topic of focus due to the difficulty of targeting medical interventions with small or large molecules alone. As small molecule drugs are designed and tested, an incredible number of possible candidates are removed from consideration due to issues involving poor pharmacodynamics or kinetics (1). A similar issue exists in larger molecular drugs based on DNA, RNA and proteins. Studies involving the direct injection of plasmid DNA and smaller strands of RNA have shown that nucleases in blood serum destroy these drugs in a highly efficient manner (2). As such, nucleic acids cannot be delivered into the body without substantial help. Nucleic acid analogues have been used to overcome blood instability issues by being resistant to nucleases (3). However, the nucleic acid analogue approach still suffers from issues involving delivery into cells. When foreign protein drugs are delivered into the body, they are usually targeted by the humoral immune system (4). For example, patients with haemophilia A and B receiving injections of blood coagulation factors frequently develop neutralizing antibody responses which in many cases render the treatments useless with time (5). Although incredible genetic discoveries in various medical fields have been made over the last decade and a half, the lack of a practical delivery method for large molecules renders this data largely unusable. As a result, years of work have been put into designing methods to solve the issue of large molecule delivery. These methods mostly include the use of modified recombinant viruses and non-viral liposomes (6). Although viruses have shown promise under some medical circumstances there are ongoing issues of toxicity, target specificity or cell tropism, and ethical concerns associated with their use (7). Virus particles also become targets for the humoral immune system, greatly limiting their use to a narrow time window before neutralizing antibodies arise (8). If treatments are unsuccessful in this time window, further virus injections are quickly eliminated by the immune system. Non-viral methods based on liposomes have been seen as the safer alternative to viral delivery of large molecules. Efforts involving liposomes have been classically hampered by low efficiency of delivery, issues with vehicle loading efficiency, and practical issues involving preservation of structure during storage (3, 9).

Liposome Design Challenges with Delivery Efficiency, Drug Loading, and Structure Preservation Liposomes are normally single phospholipid bilayer bubbles which separate the drug inside from the hostile environment outside. Incredible arrays of methods have been used to modify the outside of liposomes in order to make them more targetable, more delivery efficiency, and more structurally stable. Efforts to target the liposome via linked antibodies/peptides to the surface of the desired cell type for endosome uptake are known (10). When the targeted cell envelopes the liposome, the newly formed endosome continues through a natural process which degrades the contents for use as food sources. During this process, the contents of the liposome are freed into the cytoplasm usually via the destruction of the endosome membrane. The release of late-endosomal or lysosomal contents into the cytoplasm is a source of cytotoxic effects of non-viral vectors (11). Now in the cytoplasm, the liposome contents are then free to act in the local environment. However, targeting the nucleus in non-mitotic cells is impeded by the dual-bilayered nuclear membrane barrier and the nuclear pore complex. Some have attempted to address this issue by introducing transcription factor binding sites into the therapeutic DNA drug (12). Transcription factors bind to target sites on the DNA drug and help to shuttle it to the nucleus during signal transduction. These efforts have increased the rate of uptake into the nucleus; however the efficiencies of liposome therapy still remain much lower than robust viral methods. The movement of nucleic acids into the nucleus from the cytoplasm is dependent on the length of the strand due to the need for this molecule to fit though the narrow nuclear pore complex.

Another additive to the liposome is the use of membrane fusion proteins. These proteins have been employed to allow liposomal membranes to fuse with the cell's plasma membrane. This method unloads the contents of the cell into the cytoplasm without breaking down endosomal barriers, avoiding considerable cytotoxicity (13, 14). In effect, the liposome can be loaded with any sized nucleic acid for delivery into the cytoplasm. However, nucleic acids delivered by membrane fusion proteins into the cytoplasm are still subject to the "thread in needle" efficiency of the nuclear pore complex.

The efficiency of drug loading and structure retention can also be of concern in the practical implementation of liposomal drug delivery. In simplest terms, a tiny bubble can be formed easily, but keeping it intact during drug loading and long term storage has provided challenges (9). When a normal liposome mixture is extruded to produce the desired single membrane unilamellar format, the subsequent drug loading and storage can become a problem. Freeze dried liposomes do not retain their original shape and size upon addition of soluble drug. Since their shape and size are relevant to the desired delivery function, liposomes should be shape-stabilized prior to storage (9). In order to address this issue, some have used complexing agents to harden the liposome membrane/structure. This allows liposomes to be formed with one membrane, to be fixed in that structure through a complexing agent, freeze-dried, and then loaded by hydrodynamic force (drug in water) (15). This allows a liposomal drug to be assembled and stored as a freeze dried mixture and loaded efficiently prior to use. Although, the efficiency of the liposome assembly process is enhanced, surface hardening and complexing chemistry is incompatible with the use of membrane fusion protein methods. This is because the modified liposome surface has no fluidity or opening within which a membrane fusion protein could function. This lack of fluidity limits externally hardened liposomes to a delivery efficiency which is dependent on endosomal escape.

Self-Assembling Structures Based on DNA Complementary Binding

In the past decade, researchers have begun to explore the assembly of complex structures at the nanometer scale. Nanotechnology often employs information encoding DNA to design structures with preset parameters (16). Structures often are designed by linking ssDNA to effector molecule(s) and then assembled by the complementary base pairing innate to dsDNA. These techniques coupled with lithographic chip and microfluidics gives the user the capability to create devices that can perform a wide array of tasks from sensing DNA sequences, to the step wise assembly of small machines (17). The use of nanotechnology in the synthesis of drugs is still in its infancy. To date, only a few labs have considered the use of DNA in the synthesis of drug delivery vehicles. These interests surround designing DNA to form three dimensional structures which are then placed in the body (18). However, most of these techniques do not account for the body's innate ability to clear foreign DNA from the blood stream. Liposomes, which are used to hide DNA cargo from destructive blood enzymes, have not been designed with a self assembling platform.

There is a need in the art for a liposome and method of preparing a liposome with an internal structure that is amenable to the addition of surface proteins with a fluid membrane, and while still being stable during a freeze thaw cycle. In addition, there is a need in the art for an internal structure in a liposome that could aid its overall structural stability by keeping membrane layers from mixing and moving during both the freeze-drying and storage. Further, there is a need in the art for a liposome having an internal structure that could also aid in the synthesis of the overall vehicle with multiple bilayers and by allowing effector proteins to bind to the scaffold itself, and the product of which could be capable of taking any sized molecule and placing in any sub-cellular address in the body.

BRIEF DESCRIPTION OF THE DRAWINGS

Reference will now be made, by way of example, to the accompanying drawings which show example embodiments of the present application, and in which.

SUMMARY OF INVENTION

Figure 1A:
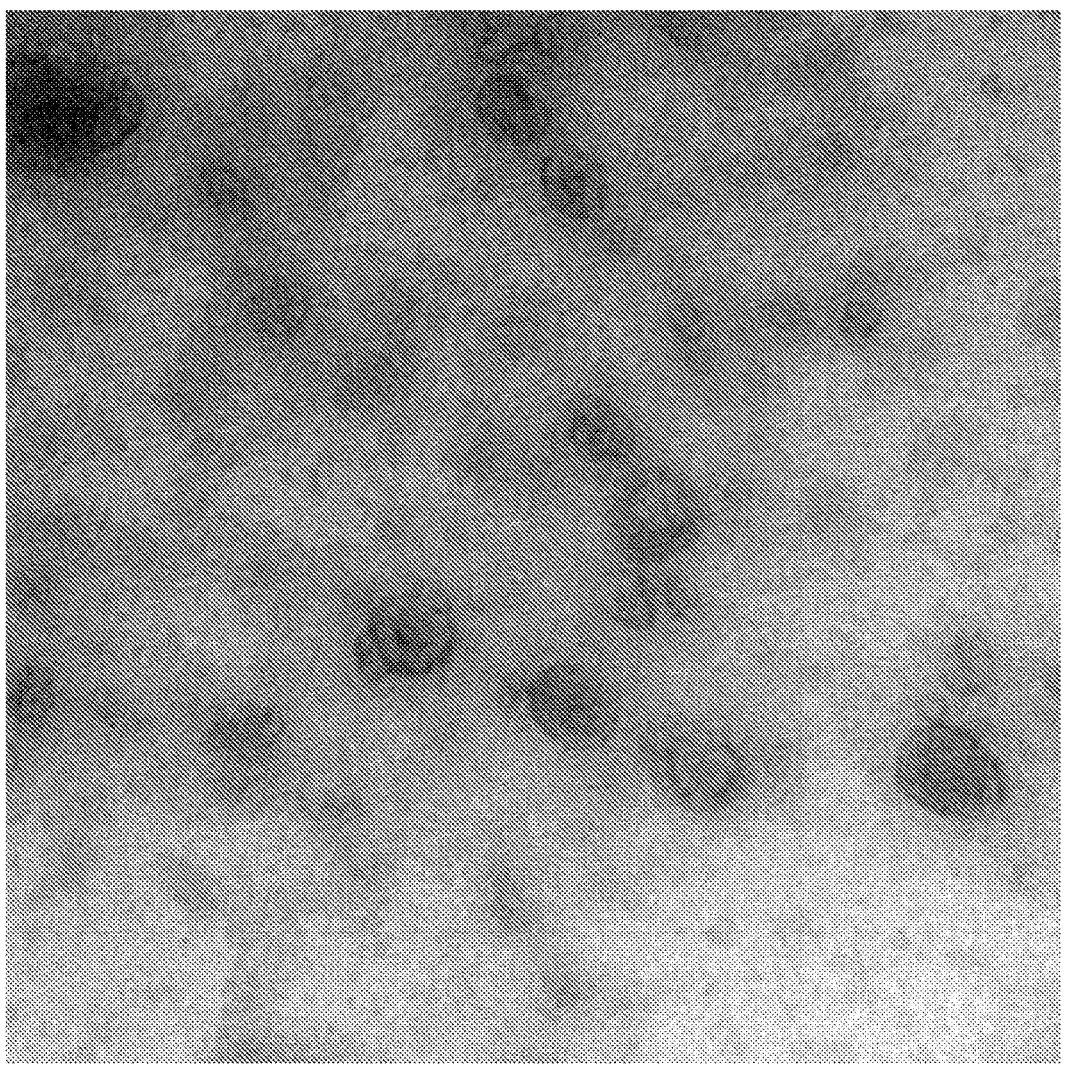
FIG. 1A is an electron micrograph image of negative control liposomes.
Figure 1B:
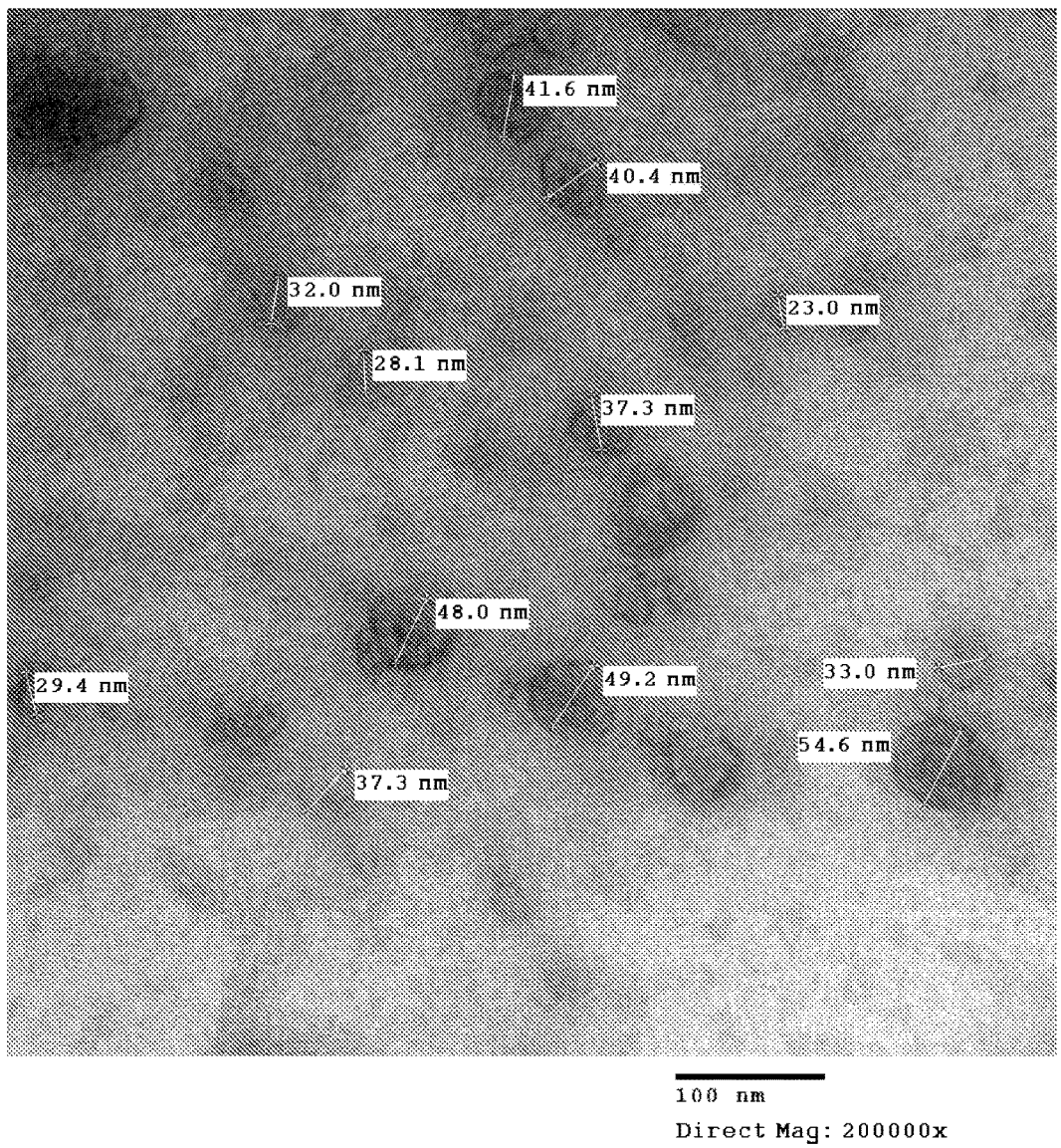
FIG. 1B is an electron micrograph image of the negative control liposomes of FIG. 1A with annotations indicating size of the liposomes.
Figure 1C:
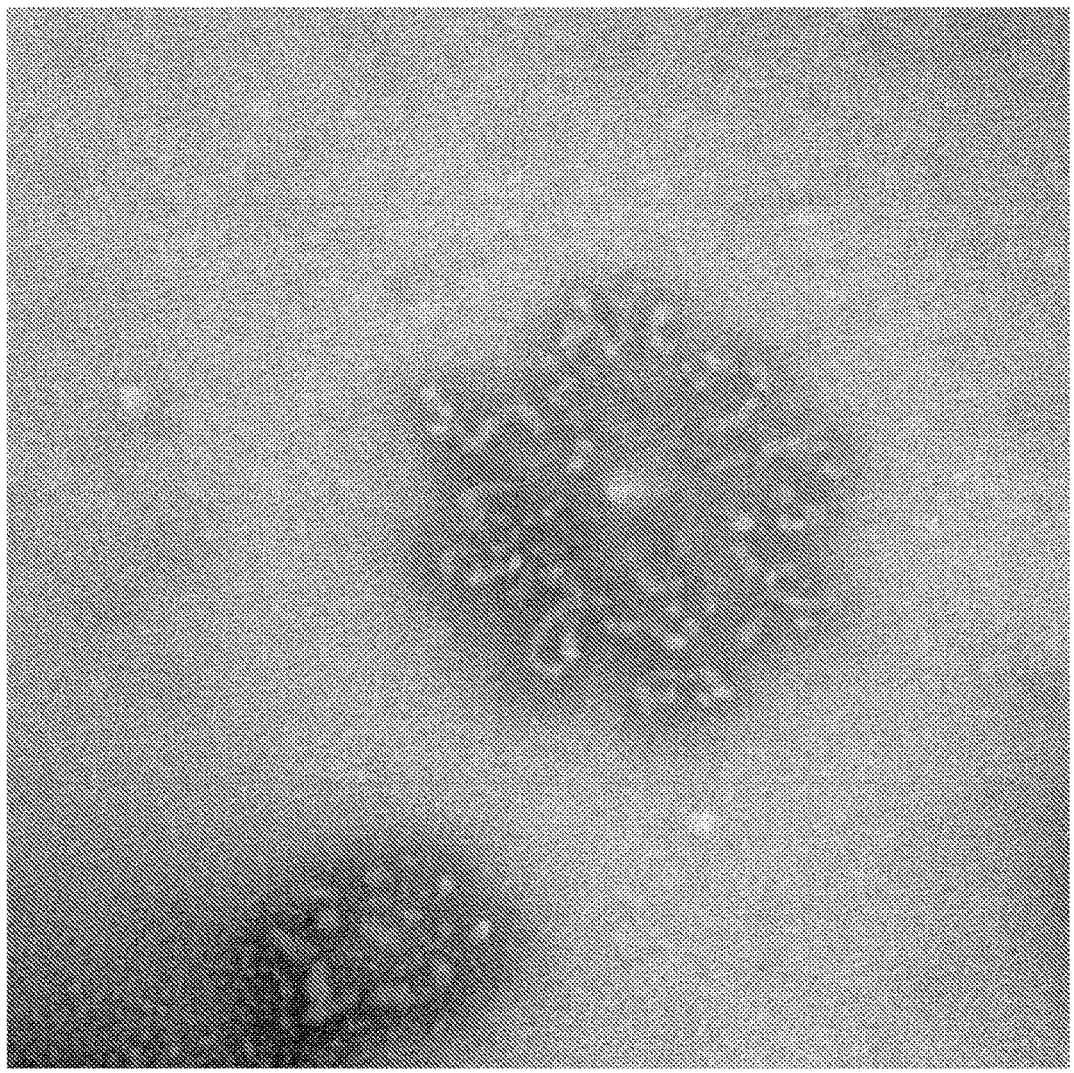
FIG. 1C is an electron micrograph image of internal Structured Self Assembling Liposome (ISSAL) liposomes.
Figure 1D:
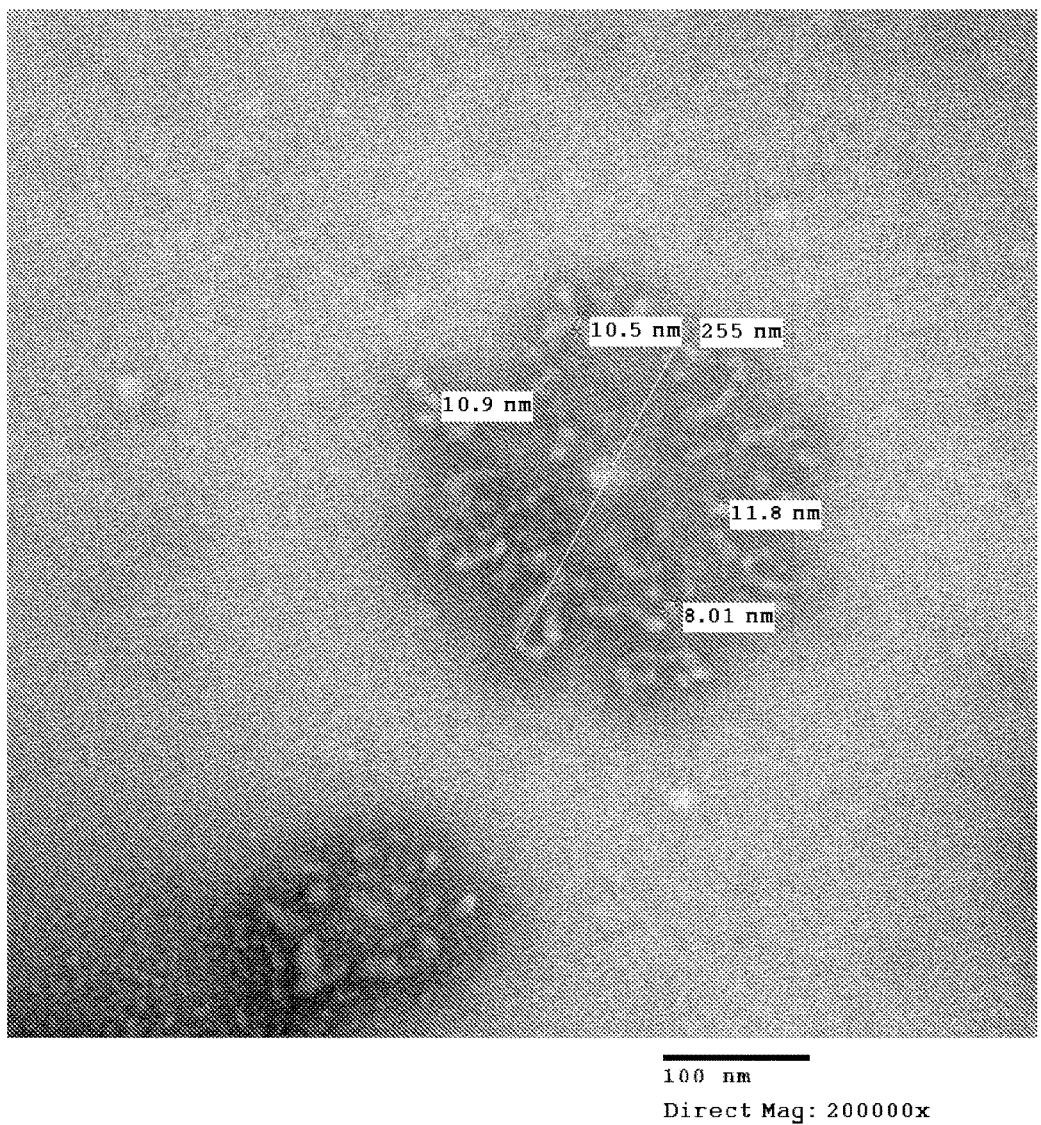
FIG. 1D is an electron microscopy image of the ISSAL liposomes of FIG. 1C with annotations indicating size of the liposomes.

In one aspect, the specification relates to an internal structured self assembled liposome (ISSAL), containing:
a nuclear core molecule or complex including a first affinity enhancing molecule; and
a liposome encompassing the nuclear core molecule or complex, the liposome containing a lipid bilayer containing a phospholipid-affinity enhancing complex having a phospholipid coupled to second affinity enhancing molecule, wherein the second affinity enhancing molecule couples to the first affinity enhancing molecule.

In another aspect, the specification relates to a method of forming an internal structured self assembled liposome containing a nuclear core molecule or complex including a first affinity enhancing molecule; and a liposome encompassing the nuclear core molecule or complex, the liposome containing a lipid bilayer containing a phospholipid-affinity enhancing complex having a phospholipid coupled to second affinity enhancing molecule, wherein the second affinity enhancing molecule is coupled to the first affinity enhancing molecule, the method including the step of mixing the nuclear core molecule or complex with the phospholipid-affinity affinity enhancing complex.

In a further aspect, the specification relates to use of an internal structured self assembled liposome, in the treatment of a disease, the internal structured self assembled liposome containing a nuclear core complex having a nuclear core molecule or complex including a first affinity enhancing molecule; and a liposome encompassing the nuclear core molecule or complex, the liposome containing a lipid bilayer containing a phospholipid-affinity affinity enhancing complex having a phospholipid coupled to second affinity enhancing molecule, wherein the second affinity enhancing molecule is coupled to the first affinity enhancing molecule.

In still another aspect, the specification relates to a method of delivering an active pharmaceutical ingredient to a patient in need thereof, containing the step of providing the active pharmaceutical ingredient in an internal structured self assembled liposome containing a nuclear core molecule or complex including a first affinity enhancing molecule; and a liposome encompassing the nuclear core molecule or complex, the liposome containing a lipid bilayer containing a phospholipid-affinity affinity enhancing complex having a phospholipid coupled to second affinity enhancing molecule, wherein the second affinity enhancing molecule is coupled to the first affinity enhancing molecule.

In another further aspect, the specification relates to method of treatment of a disease, including the step of providing to a patient in need thereof, a active pharmaceutical ingredient in an internal structured self assembled liposome including a nuclear core molecule or complex including a first affinity enhancing molecule; and a liposome encompassing the nuclear core molecule or complex, the liposome containing a lipid bilayer containing a phospholipid-affinity affinity enhancing complex having a phospholipid coupled to second affinity enhancing molecule, wherein the second affinity enhancing molecule is coupled to the first affinity enhancing molecule.

In another still further aspect, the specification relates to a pharmaceutical composition containing an internal structured self assembled liposome containing a nuclear core molecule or complex including a first affinity enhancing molecule; and a liposome encompassing the nuclear core molecule or complex, the liposome containing a lipid bilayer containing a phospholipid-affinity enhancing complex having a phospholipid coupled to second affinity enhancing molecule, wherein the second affinity enhancing molecule is coupled to the first affinity enhancing molecule; and a pharmaceutically acceptable excipient.

In still another further aspect, the specification relates to a kit, containing:

an internal structured self assembled liposome containing a nuclear core molecule or complex including a first affinity enhancing molecule; and a liposome encompassing the nuclear core molecule or complex, the liposome containing a lipid bilayer containing a phospholipid-affinity enhancing complex having a phospholipid coupled to second affinity enhancing molecule, wherein the second affinity enhancing molecule is capable coupled to the first affinity enhancing molecule; and instructions for use.

DESCRIPTION OF EXAMPLE EMBODIMENTS

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, only embodiments of the materials and methods are described herein.

The examples of molecules used in the assembly of this structure are examples of molecules which can form the internal structure overall and should not be considered as exclusive embodiments of this invention or in any way limiting the scope of invention. Many other molecules can be combined covalently to form similar structures to those examples listed and are equally viable examples of this ordered self-assembling internal structure liposome.

The assembly of the liposome internal structure begins with the production of a "nucleus" molecule/complex for the core. This is the point upon which the rest of the liposome is assembled in stages. The nuclear core molecule or complex is linked (in one example embodiment and without limitation, covalently linked) to first affinity enhancing molecules which provide the assembly point for the first surrounding lipid bilayer. An example of this nuclear core complex could be to covalently link micelle forming phospholipids to the 5' phosphate groups of ssDNA. In this example, the nuclear core structure can be roughly spherical and capable of binding multiple ssDNA groups via a 5' phosphate. Another example of a nuclear core molecule could be a group of oligonucleotides which when combined in solution make a three dimensional pattern with free ssDNA ends.

The following is an example of the assembly of the first lipid bilayer in the liposome. Phospholipids, which have been covalently linked at the hydrophilic end to a second affinity enhancing molecule, are used to bind to the core complex. An example of this could be to link the terminal $NH_2$ group of phosphatidylethanolamine (PE) to the 5' phosphate group of ssDNA to create a phospholipid-ssDNA adduct (pl-ssDNA). The first bilayer is formed upon mixing phospholipids and pl-ssDNA with the ssDNA-nuclear core complex. This assembly of the first bilayer is helped by the specific association of dsDNA affinity complementary binding. In this example, the pl-ssDNA on the outer surface of the first liposome bilayer provides the structural basis for assembling further bilayers. As such, liposomes bilayers are constructed in stages. With each sequential stage, different soluble drugs or varying membrane functionality can be applied. The entire structure, when assembled, could be comparable to a "3D wheel" where the dsDNA functions as structural "spokes".

For the implementation of this design, another example could be to use affinity proteins, polypeptides, or nucleic acid analogues in place of ssDNA at all points in the above assembly. In this way, the nuclear core is linked to the first bilayer via protein-protein specific interaction. At this point, protein subunits could face outward on the liposomal surface for assembly of the next lipid bilayer. In the same way, the nuclear core molecular or complex need not be a micelle; rather a generally spherical molecule can be used with outward functional points. Another example of a nuclear core complex could be a small compact protein with modified surface residues linked to affinity based molecules, such as ssDNA. The overall liposome structure could still resemble a layered 3D wheel in which molecules of DNA or polypeptide function as spokes to keep and align lipid bilayers around a central core.

The overall use of these internal structured self-assembling liposomes could be to place any soluble molecule into any sub-cellular location in the body. Sub-cellular targeting can be accomplished by adding specific membrane affinity (ie. surface antibodies) and membrane fusion properties to each liposome bilayer stepwise during assembly. As such, the outer bilayer binds and enters the surface of a targeted cell in the body and the subsequent bilayers underneath are targeted to other membrane layers within the cell (ie. nuclear envelope, mitochondria, golgi complex, etc). Insoluble drugs can also be mixed in the hydrophobic region of phospholipid bilayers during their assembly.

Soluble proteins which are linked to ISSAL ssDNA can be incorporated into the complex via base pair affinity. Single span membrane proteins such as various membrane fusion proteins which are stabilized in solution via solubilising domains can also be linked to ssDNA (19). These single span membrane proteins could then be added to the existing scaffold of pl-ssDNA. The net effect could be that the membrane proteins are ordered in the correct ecto/endo domain orientation in the bilayer. As the bilayers are assembled stepwise, unique affinity targeting and membrane fusion can be applied to separate layers. Since the DNA scaffold keeps the bilayers from interacting, any membrane fusion events would have to begin at the liposomal outer surface instead of between interior bilayers. In such a way, the first bilayer could breach the plasma membrane of a cell and the subsequent bilayers could be targeted to breach the nuclear envelope layers.

Layers in the liposome internal structure are severed via specific endonuclease or protease activity. This is done by dividing one regime into two separate but equivalent parts. Each of the two formulations contains the enzymes to break the structural components of the other formulation. This avoids the breakdown of the internal structure components of the liposome prior to the correct delivery to each subsequently targeted membrane compartment. When the final bilayer is assembled, the excess DNA on the surface is cut via recombinant nuclease activity and the liposomes purified.

In summary, a complex multi-layered self assembling liposome could be loaded with any soluble or insoluble molecule(s) and its contents released in any sub-cellular address within the body. This can help to address the issues of liposome delivery efficiency with the use of surface antibodies and membrane fusion proteins. The internal structural supports also greatly decrease the movement of membranes during drug loading and storage. This design can also allow for the ability to unload even chromosome sized molecules into targets like the nucleus or mitochondria.

Production and Purification of Long Chain ssDNA

Currently, it can be challenging to synthesize long chain ssDNA with high quality and quantity in an inexpensive manner. The following method was adapted to provide one route, although routes may be also possible, for synthesizing sufficient inexpensive long chain ssDNA for use in ISSAL constructs.

Iron superparamagnetic nanoparticle resins can be used for the large scale, batch format separation of large molecules such as long chain ssDNA. The following method was adapted from Bumb et al. 2008 (20). These nanoparticles are an example of known design that could aide in the extraction of ISSAL components and is not required for ISSAL assembly or function. Briefly, iron nanoparticles are created by reacting $Fe^{2+}$ and $Fe^{3+}$ ions with concentrated ammonia. The particles are washed with magnetic separation and then washed with 2M $HNO_3$ to convert the surface charge from negative to positive. The particles are then washed with magnetic separation to remove most of the concentrated acid. After stabilizing the pH at 2.5 with NaOH and $HNO_3$, the particles are surface stabilized by saturation with citrate ions. The particles are then washed and pH stabilized at 6.0. The particles are then silica coated by reacting with a mixture of tetraethylorthosilicate (TEOS) and (3-amino-propyl) triethoxysilane in ethanol, using triethylamine as a catalyst. The amino groups on the surface of the particle are then ready to be linked to ssDNA with a water soluble cross linker such as 1-ethyl-3-(3-dimethylaminopropyl) carbodiimide (EDC).

Figure 2:
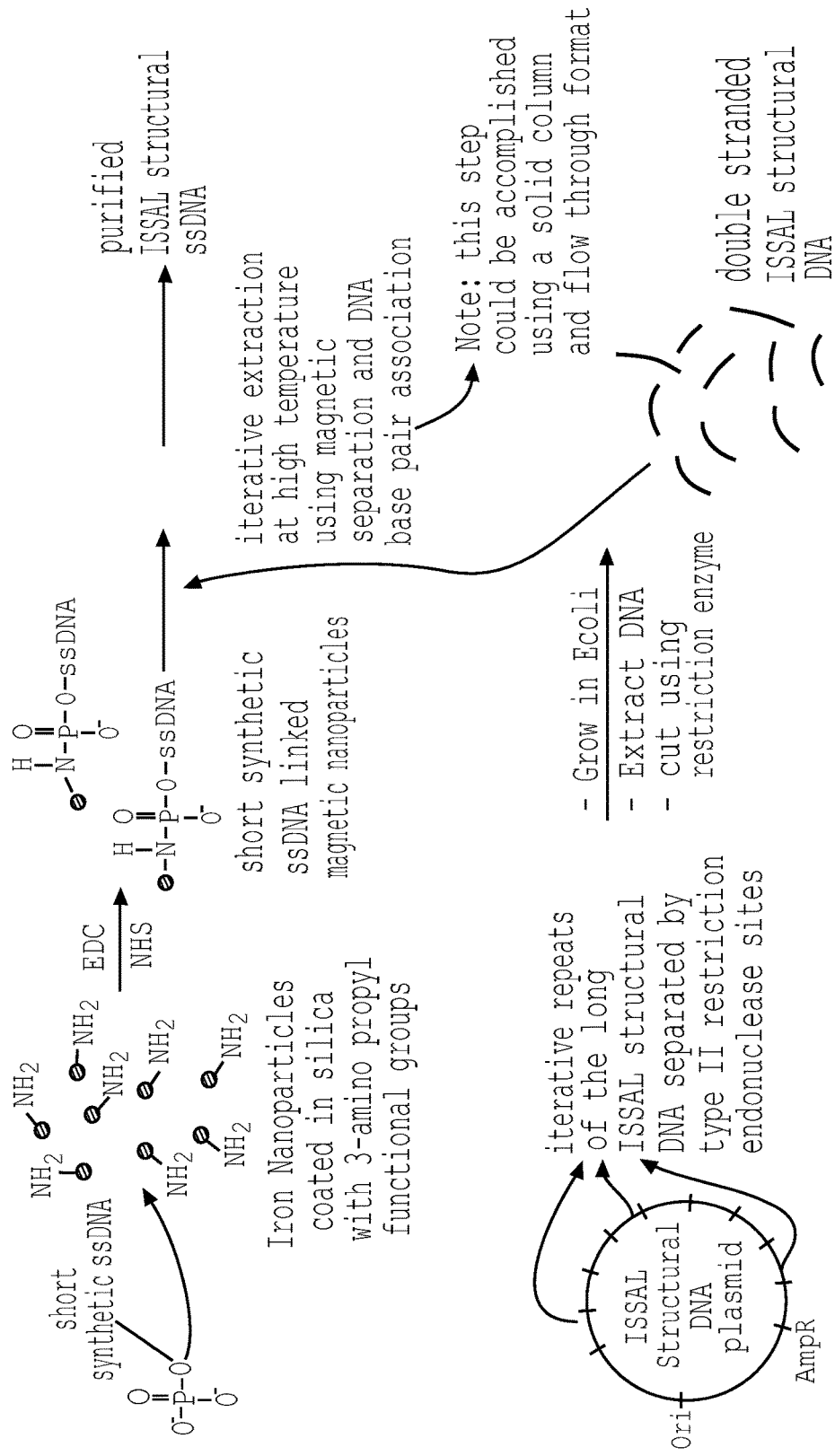
FIG. 2 is an example of synthesis of long single stranded DNA for ISSAL structural assembly.

To separate long chain ssDNA, a complementary base sequence can be added to the surface of the nanoparticles. FIG. 2 discloses how longer ISSAL ssDNA is made and purified.

stranded DNA is then separated with iterative high temperature annealing to complementary ssDNA bound magnetic resin.

In order to create the first batch of separating nanoparticles, the complementary ssDNA can be synthesized using standard synthetic techniques. The synthetic ssDNA is crosslinked to surface amine groups of silica coated iron nanoparticles with EDC in water. When the reaction is complete, the solution is washed with water via magnetic separation. Longer ssDNA can now be purified by strategically controlling the temperature of annealing and magnetic separation. This is made possible because the iron nanoparticles are not sensitive to heat ranges between 4° C. and 200° C. (20).

Long chain DNA to be used in the synthesis of self assembling liposomes is grown within high copy number plasmids. These plasmids are harvested inexpensively from bacteria such as *E. coli*. These high copy number plasmids contain the desired sequence in multiple repeats for added efficiency. The double stranded plasmid DNA is purified from bacteria using the common alkaline lysis technique. Following a basic DNA purification with a silica substrate, the DNA is cut with restriction enzymes designed to remove the plasmid back bone and separate individual desired sequences. This digested mixture is then applied to the iron nanoparticle ssDNA conjugates for separation. Separation is achieved by high temperature annealing followed by magnetic separation. The separation efficiency of short chain DNA conjugated nanoparticles can be low at first. However, after multiple separations a small fraction of purified complementary DNA can emerge. This small amount of purified long chain ssDNA is then used to create a new and superior batch of iron nanoparticle ssDNA conjugates. This process is repeated until the separated ssDNA is completely free of contaminants. This process also applies to any other Scheme 1. Synthesis of long single stranded DNA for ISSAL structural assembly. Double stranded DNA is grown in *E. coli* via high copy number plasmids. These plasmids are then cut with restriction endonucleases. The double stranded DNA is then separated with iterative high temperature annealing to complementary ssDNA bound magnetic resin.

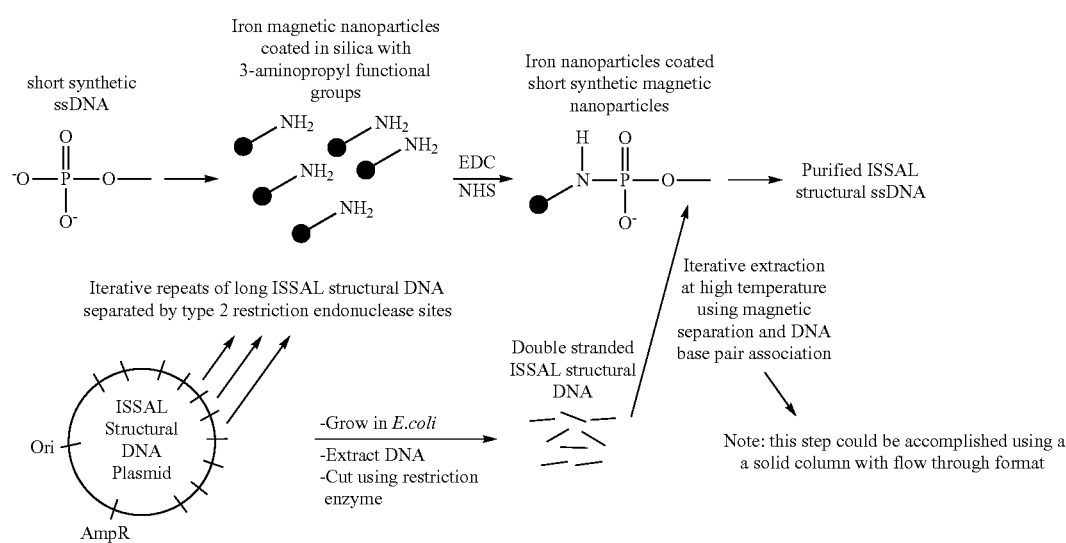

FIG. 2 shows the synthesis of long single stranded DNA for ISSAL structural assembly. Double stranded DNA is grown in *E. coli* via high copy number plasmids. These plasmids are then cut with restriction endonucleases. The double complementary ssDNA to be separated. The method can allow avoidance of harsh chemical treatment of the original dsDNA to separate ssDNA strands based on GC/AT ratio differences. This technique is also not biased to any base pair configuration, can be inexpensive and scalable to large batch size. The iron nanoparticle ssDNA conjugates can also be reused many times. Alternatively, a purified preparation of ssDNA could be bound to a solid column matrix. This could allow for high temperature liquid chromatography of the desired ssDNA instead of magnetic separation.

Synthesis of Pl-ssDNA Subunits

Long chain ssDNA is purified with the above method and placed in solution with EDC and N-hydroxysuccinimide (NHS). Next, PE is added to the ssDNA mixture. After the reaction is complete, the components are purified to remove unwanted products. The PE, ssDNA, and pl-ssDNA are separated using a large column format containing covalently bound complementary ssDNA. Initially the ssDNA and pl-ssDNA are bound to the column. Then the PE is washed away using an increasingly organic phased buffer. The ssDNA and pl-ssDNA are then eluted at high temperature and put through a second column with a hydrophobic medium. The ssDNA will not bind to the hydrophobic column and is eluted. The pl-ssDNA is then eluted by increasing the organic eluant phase. The pl-ssDNA is then dried by solvent evaporation and stored in the dark under nitrogen. Note that any trace contaminants of PE or ssDNA should not be problematic for the assembly of ISSALs.

of this is monoacyl phospholipids such as lysophosphatidylethanolamine (LPE). LPE can be made by reacting purified PE with a soluble phospholipase A2. This produces a LPE with the second carbon of the glycerol chain deacylated. LPE, which is positively charged, is purified to remove free fatty acids. This is done by binding to a cation exchanging hydrophobic mixed mode resin. Free fatty acids will not bind and are carried away in the wash. The resulting mixture is of LPE and unreacted contaminant PE. These PE contaminants can be ignored if they are in low enough concentrations as they can have little impact on the formation of micelle structures. The molar ratio of this contaminant should not react higher than 20 LPE to 1 PE. LPE can be dried and stored in the dark under nitrogen.

The ISSAL ssDNA is mixed with LPE and allowed to react in the presence of EDC and NHS soluble crosslinking reagents. The resulting mixture of LPE, ssDNA, LPE-ssDNA adducts, EDC and NHS can be separated and purified as described above with pl-ssDNA. Purified ssDNA-LPE should be stored dry in the dark under nitrogen.

Assembly of ISSAL Subunits

Figure 3:
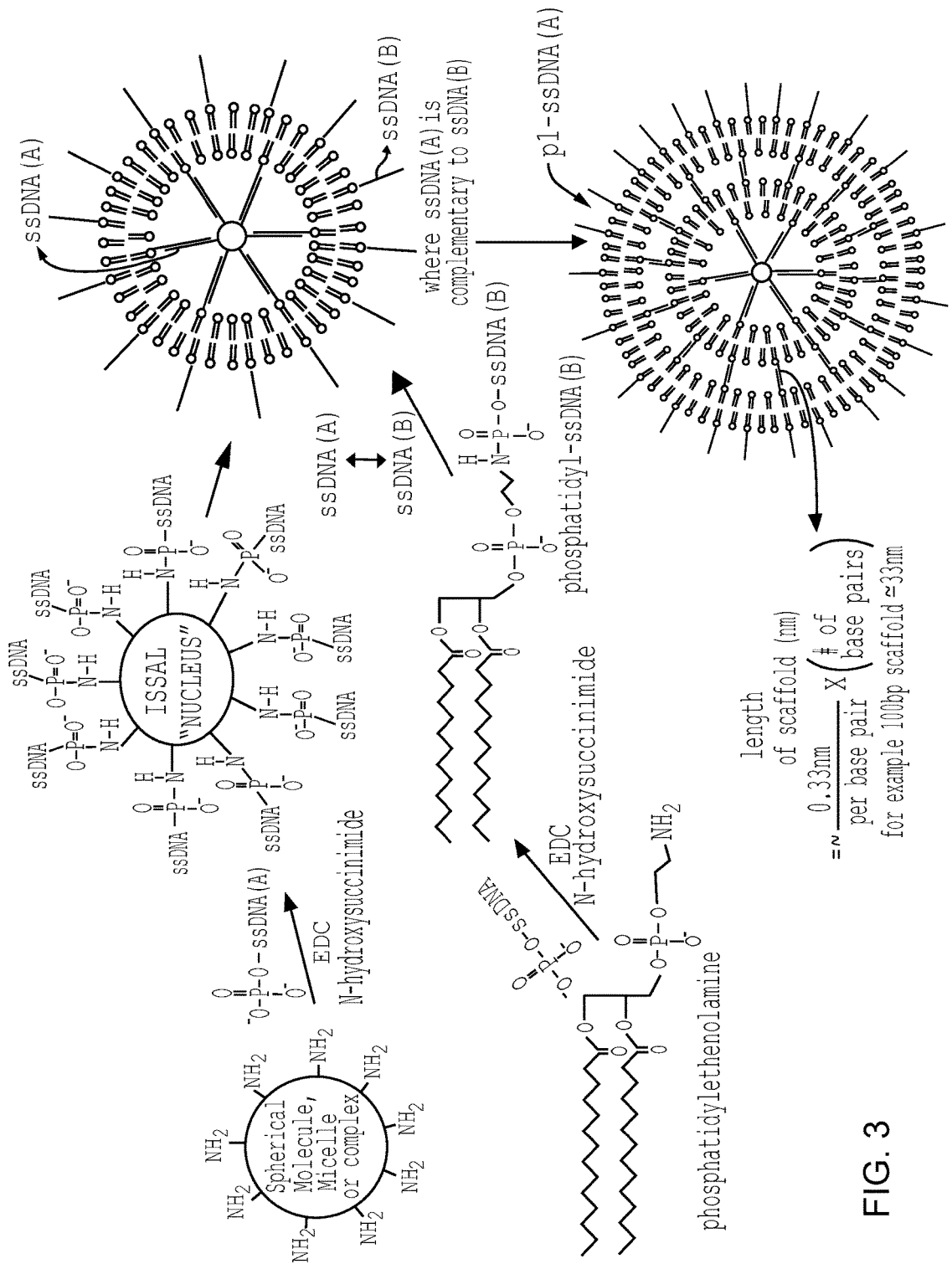
FIG. 3 is an example of synthesis of phospholipid-single stranded DNA adducts (pl-ssDNA), the production of ISSAL "nuclei" structures, and the stepwise assembly of internal structured self assembling liposomes.

The assembly of ISSAL in solution is a step wise process under on and off column conditions. Columns conditions involving iron nanoparticle ssDNA conjugates are used to simplify purification of ISSAL during synthesis and to minimize the occurrence of contaminants. FIG. 3 illustrates how the ISSAL assembly proceeds.

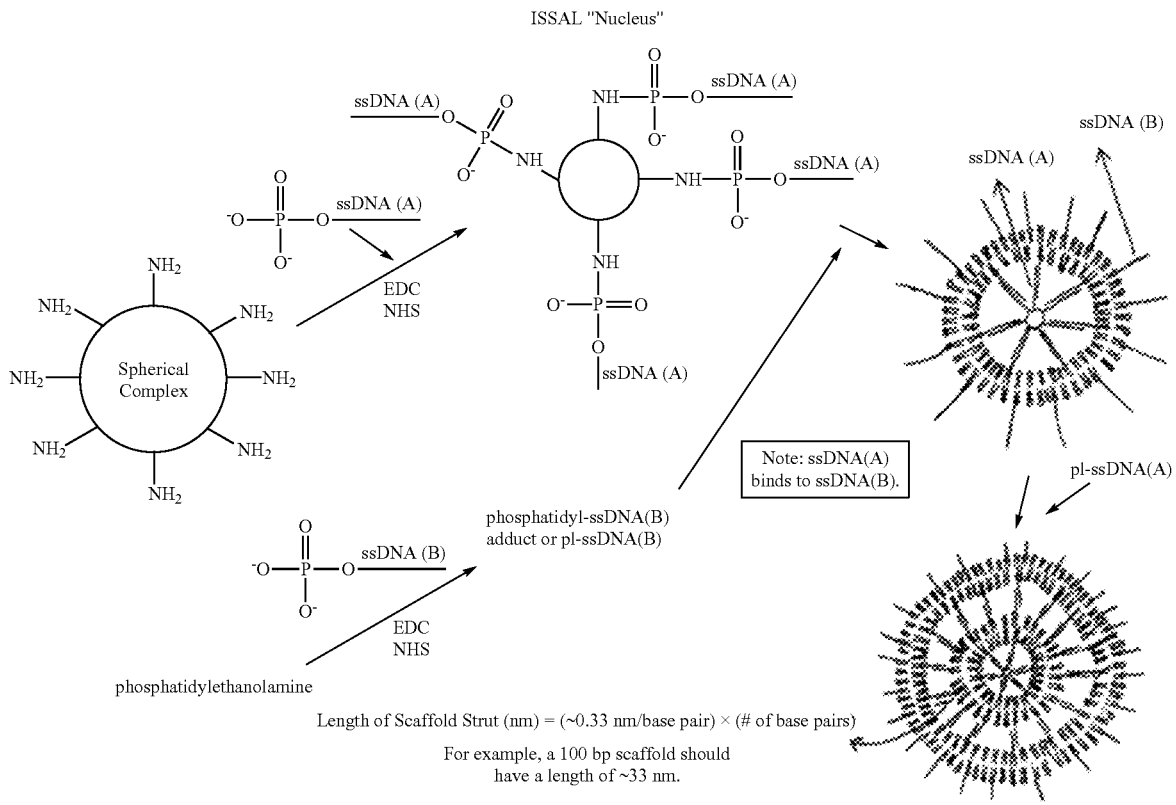

Scheme 2. Synthesis of phospholipid-single stranded DNA adducts (pl-ssDNA), the production of ISSAL "nuclei" structures, and the stepwise assembly of internal structured self assembling liposomes.

Length of Scaffold Strut (nm) = (~0.33 nm/base pair) × (# of base pairs)

For example, a 100 bp scaffold should have a length of ~33 nm.

Synthesis of Micelle-ssDNA Nuclei Subunits

Micelles are a mixture of spherical amphipathic molecules in water without a bilayer. Some amphipathic molecules form micelles more readily than others. On example FIG. 3 shows the synthesis of phospholipid-single stranded DNA adducts (plssDNA), the production of ISSAL "nuclei" structures, and thr stepwise assembly of internal structured self assembling liposomes.

In the first layer, there is a mixture of two different pl-ssDNA molecules. Self-assembly begins by mixing ssDNA-LPE adducts and regular LPE in water with agitation at 4° C. This forms the micelle nuclei spontaneously in solution. Micelles are the lowest energy state for this molecule and the longer the solution is shaken, the higher the entropy of the system will be when the agitation stops. The micelles in solution are then mixed with pl-ssDNA, phosphatidylcholine, PE, cholesterol, etc. in the correct mixture ratio. This forms the first lipid bilayer surrounding the nuclei. Mixtures are shaken at 4° C. to ensure the highest entropy for the system. Most will be specific for the complementary layers in the ISSAL structure, but a small proportion (30:1 molar ratio) will be specific for the iron nanoparticle ssDNA resin. Once the ISSAL intermediates are bound to the column they can be treated with any reagents compatible with the pH, temperature, ionic and solvent requirements of DNA complementary base pair binding. To avoid incorporation of iron nanoparticles in the ISSALs during assembly, the double-stranded DNA can be cut or removed by denaturation. A microfluidics "lab on a chip" assembly could also be used in place of iron nanoparticles described above.

Further bilayers are formed as above by varying the pl-ssDNA and phospholipid/cholesterol mixtures stepwise. When properly assembled, the outer layer can be predominantly of the pl-ssDNA that was last used in excess. Contaminants or spontaneous incorporation of a complementary binding pl-ssDNA into the assembly is a rare occurrence which should not affect the function of the overall ISSAL structure. Intermediate structures formed without the internal structure of the ISSAL can be less stable under cold agitation conditions and should form the lowest entropic variation over time. The rigidity of the nucleus and the shear stress stability of the ISSAL complex can determine how much agitation can be used before the ISSAL structures gain enough free energy to break apart. Higher shear stress stability is also inversely proportional to membrane fusion reactivity, once membrane fusion proteins have been added to the outer layer.

Engineering ISSAL Membrane Proteins

A functionality to be added using proteins is membrane fusion and targeting affinity. Membrane proteins can represent a challenge for standardized incorporation into complex bilayered structures. In order to overcome these difficulties, membrane spanning proteins can be adapted and engineered to incorporate correctly. For example, single transmembrane domain proteins are more likely to be solubilized then multiple transmembrane domain containing proteins. This is because of the random and unfavourable movement of the various multiple transmembrane domains in solution are more likely to cause irreversible aggregation and precipitation. Many soluble proteins, for example albumin, have considerable hydrophobic regions masked by highly hydrophilic regions. The use of solubility enhancing ecto and endo domains in protein engineering allows for similar amphipathic formations which enhance the solubility of a single pass transmembrane protein.

Figure 4:
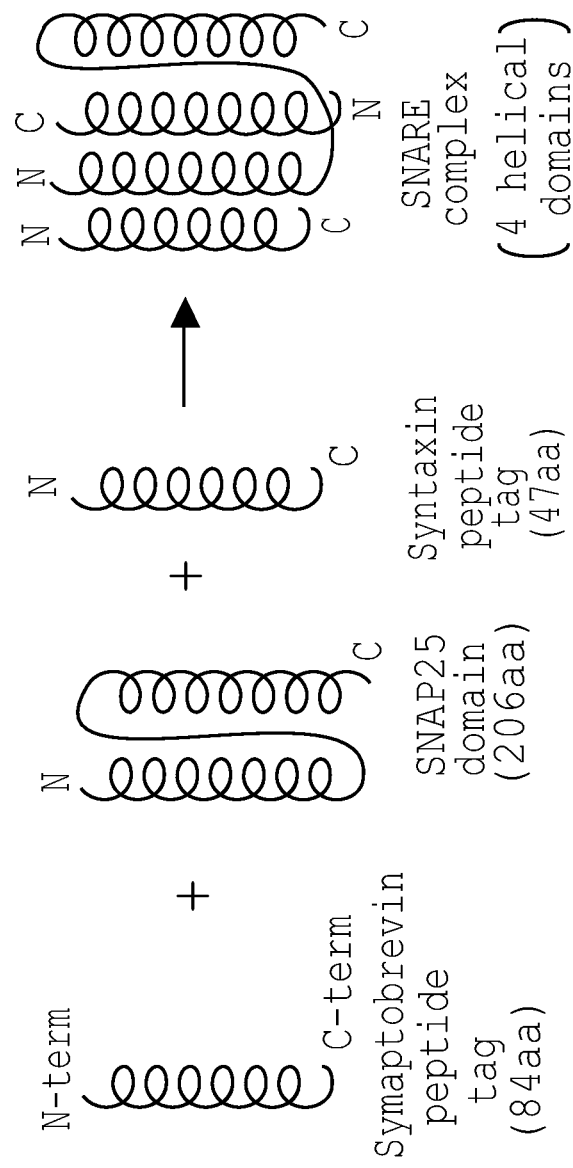
FIG. 4 is a diagrammatic illustration of the formation of syntaxin/SNAP25/synaptobrevin SNARE complexes.

In order to efficiently incorporate membrane proteins into ISSAL scaffolds, the proteins can be engineered to be readily amenable to ISSAL affinity molecules. For example, a SNAP25/synaptobrevin/syntaxin snare tag complex is a viable option for simplistic attachment of ssDNA to ISSAL engineered soluble membrane proteins (21). The snare complex described by Ferrari et al. 2010 is an example of how molecules can be linked together in a facile way. The snare complex has not been used to link liposome associated structures together. The use of a snare complex in this design is an example of molecular ligation that can be replicated with other approaches and should not be considered a mechanism that is limited to ISSAL design. FIG. 4 shows how the SNAP25 complex functions. Although SNAP25 tags do not involve covalent linkage, the association of the complex is extremely stable.

Scheme 3. Diagrammatic illustration of the formation of syntaxin/SNAP25/synaptobrevin SNARE complexes.

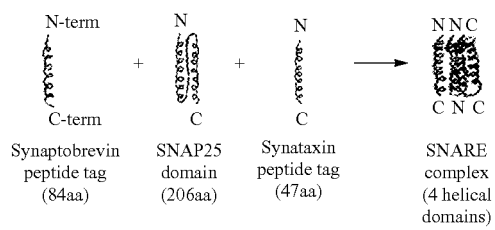

| N-term | N | N | N N C |
|---|---|---|---|
| C-term | C | C | C N C |
| Synaptobrevin peptide tag (84aa) | SNAP25 domain (206aa) | Synataxin peptide tag (47aa) | SNARE complex (4 helical domains) |

FIG. 4 is an illustration of the formation of syntaxin/SNAP25/synaptobrevin SNARE complexes.

Figure 5:
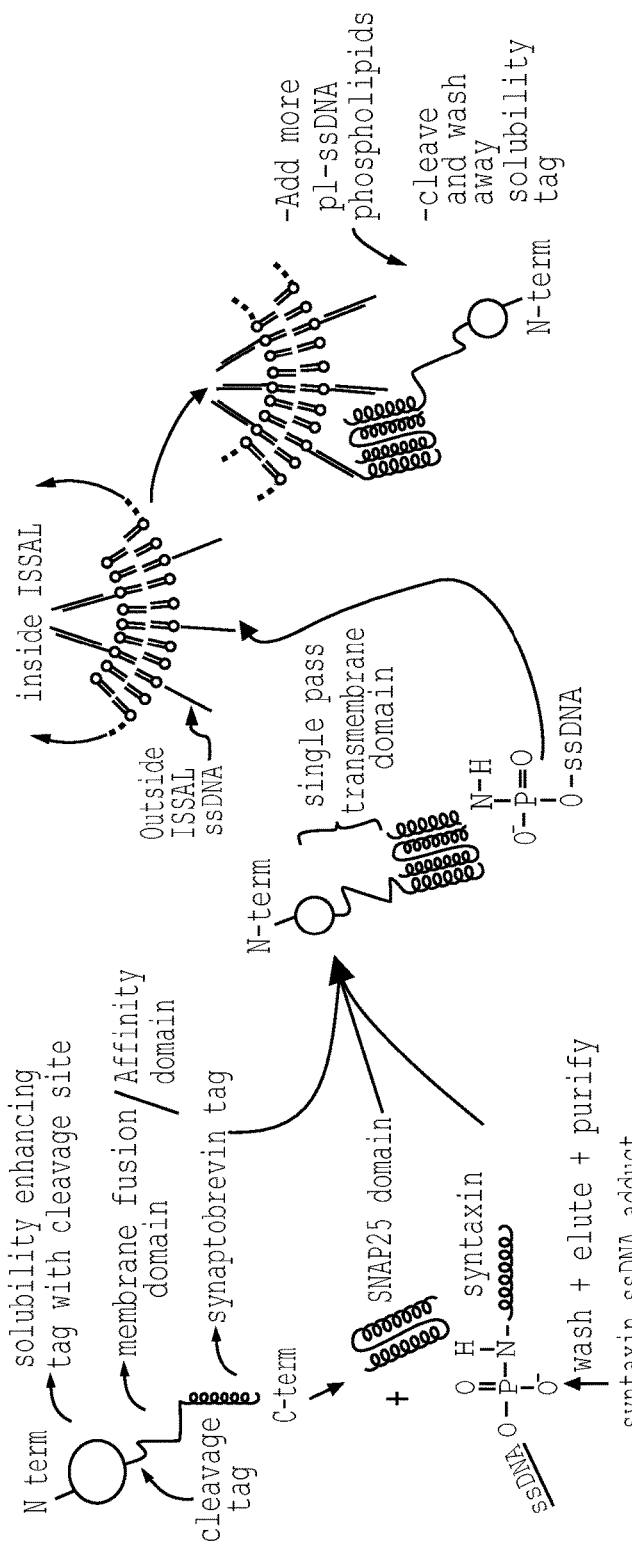
FIG. 5 is an example of the tagging of soluble membrane proteins with SNARE complexes and incorporation into ISSAL assembly.
Figure 5:
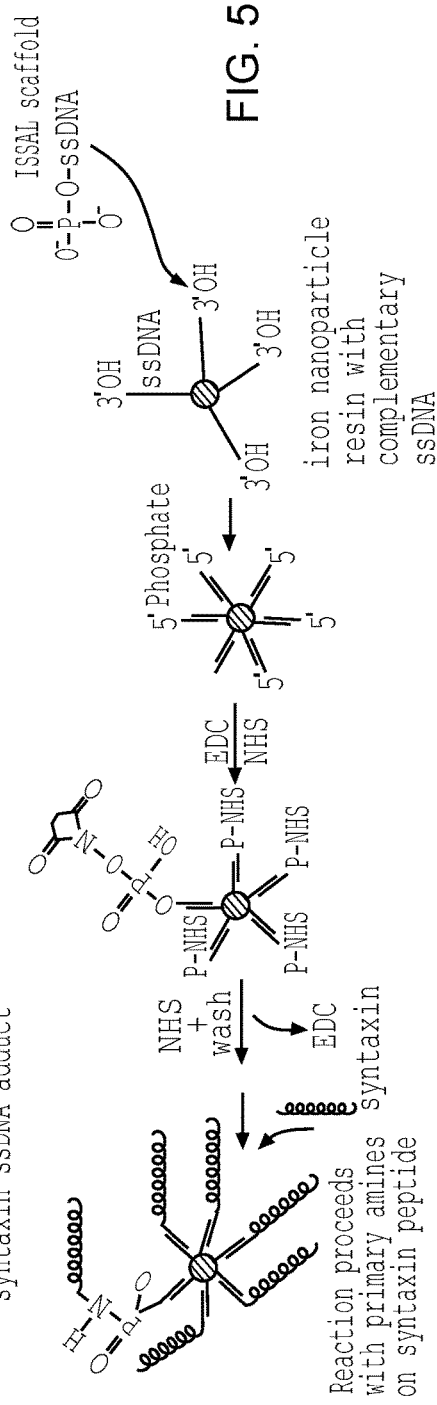

FIG. 5 discloses how the SNAP25/synaptobrevin/syntaxin complex functions as a tag for soluble membrane proteins and how these complexes are added to the ISSAL scaffold. This is done by chemically ligating the ssDNA to the syntaxin peptide. EDC readily reacts with both $-NH_2$ groups and $-CO_2-$ groups. Therefore simplistic addition of EDC directly to syntaxin peptide can cause many unwanted addition reactions in the center of the peptide with acidic side chains. Because of this, the reaction can be modified so that the ssDNA reacts first and that any unreacted EDC is removed afterward. This is done by first adhering soluble ssDNA to a complementary ssDNA iron nanoparticle resin. Then the EDC is added in the presence of NHS. This forms a stable reactive intermediate which allows for the unreacted EDC to be washed out in the presence of excess NHS. The syntaxin peptide is then mixed with the ssDNA-N-hydroxysuccinimide intermediates and allowed to react. The product is predominantly N-terminal and $-NH_2$ side chain additions via a phosphoramidate linkage to the 5' phosphate group on the ssDNA. The nanoparticle beads bound to ssDNA-syntaxin adducts are then washed to remove excess unreacted syntaxin peptide.

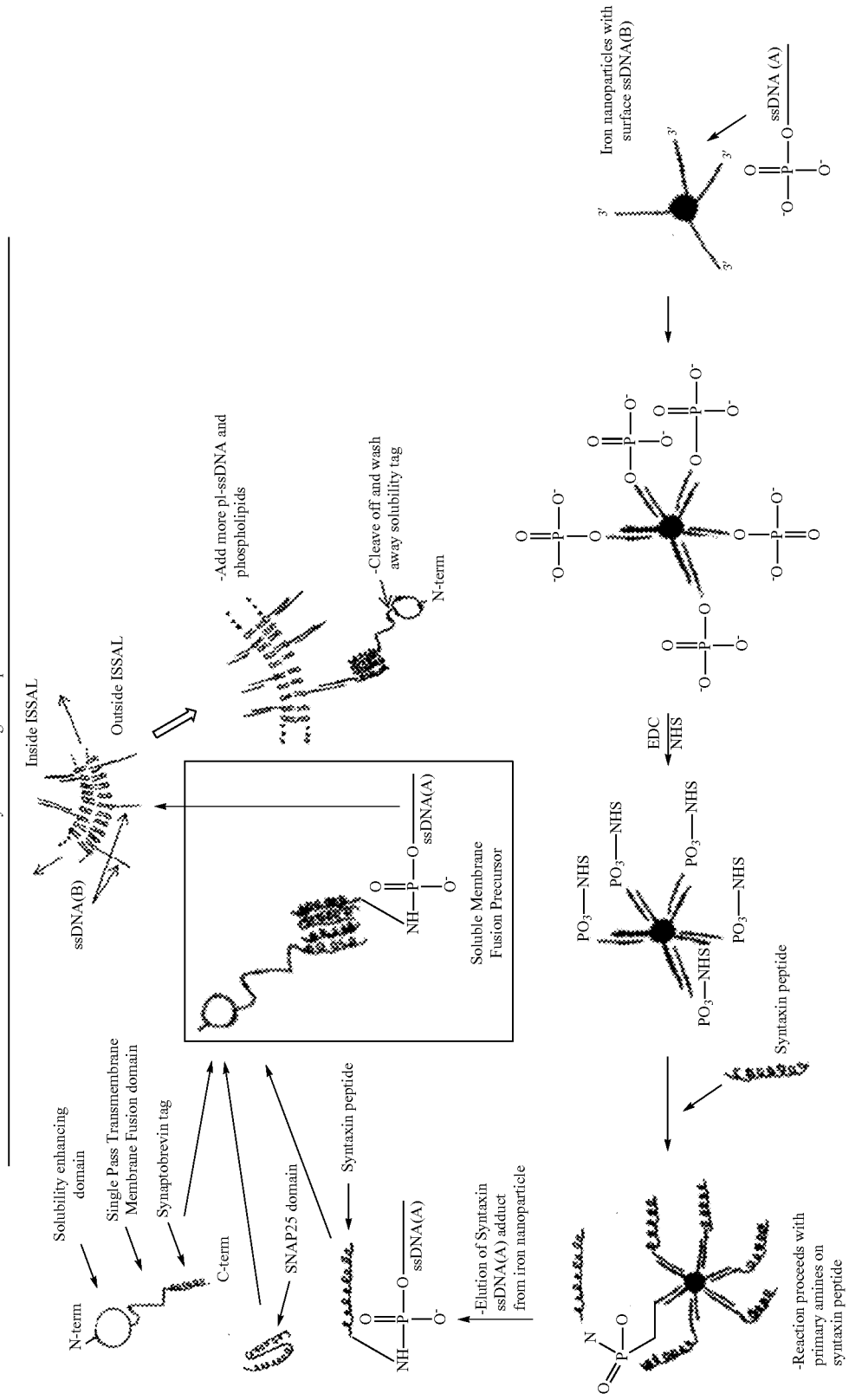
Scheme 4. The tagging of soluble membrane proteins with SNARE complexes and incorporation into ISSAL assembly. Stepwise synthesis of ISSAL allows for layers to be targeted to pass different membrane barriers.

FIG. 5 shows the tagging of soluble membrane proteins with SNARE complexes and incorporation into ISSAL assembly. Stepwise synthesis of ISSAL allows for layers to be targeted to pass different membrane barriers.

The syntaxin-ssDNA adducts need not be uniform to interact correctly with the rest of a snare complex. Therefore only simplistic purification is required. This purification can be done by making use of a histidine-6× tag applied to the end of the syntaxin peptide or by making use of a synaptobrevin/SNAP25 linked resin. Histidine-6× tags, which are normally bound to NTA-based resins, are the least expensive and fully reusable choice. The soluble membrane protein with a synaptobrevin tag is then mixed with soluble SNAP25 and ssDNA-syntaxin to form a highly stable complex. This tags the soluble membrane protein with ISSAL compatible ssDNA scaffolding. The soluble membrane proteins are then mixed with ISSAL scaffolds via DNA base pair affinity. The ssDNA interaction from the endo domain of the membrane protein can ensure that the correct outward protein orientation occurs. While the soluble membrane proteins are added, the solution can also be filled with soluble drugs for incorporation into the structure. This allows the soluble molecules to be incorporated into specific layers of the ISSAL to be delivered to different sub-cellular addresses. Insoluble drugs can be mixed into the pl-ssDNA mixture for incorporation.

Once proteins are incorporated, the ISSAL scaffolds are filled in with a pl-ssDNA/lipid mixture to form the next bilayer. Since membrane proteins can contain a highly hydrophobic region at their transmembrane domain, this portion of the protein can be more likely to be incorporated into the bilayer structure. The lowest energy state is the one in which membrane proteins are comfortably seated inside a lipid bilayer in order to meet the hydrophobicity of the transmembrane domain. Agitation in a cold system should maximize the entropy of the system.

Solubility tags on the outside of the ISSAL structure can be removed for the sake of the adaptive immune system. This is done by adhering the ISSALs via external pl-ssDNA to compatible complementary ssDNA iron nanoparticles resin and placing the mixture in a solution of site specific proteases engineered to remove the tags. Since the ISSALs in solution are "on column" they can be modified with any other system and then purified by using either heat or nucleases to release the ISSALs from the column. The external nucleic acids can also be removed from ISSAL structures due to their likely interaction with blood factors. Again, a microfluidics "lab on a chip" assembly could also be used in place of iron nanoparticles described above.

ISSAL Surface Modifications

The external structure of a liposome is critical to its function in the body. Once in the blood stream, liposomes are scrutinized for surface charge, foreign antigens, and pathogen associated molecular patterns. Many research groups have altered the surface chemistry of liposomes to make them even less visible to the immune system. For example: hyaluronic acid and polyethylene glycol have been used to modify foreign antigen recognition in viral and liposome vectors (22). These methods could also be applied to this invention using the "on column" method mentioned above. However, the functionality of membrane fusion proteins and targeting affinity should be preserved after any surface modifications or the ISSAL can become inert. It is conceivable that small sugar based polymers could be added to the surface of ISSALs. These sugar polymers, could function to hydrate the surface of the ISSAL.

Advantages of the ISSAL Design Over Other Liposomes

An ordered self assembling internal structure in a liposome allows the advantage of adaptivity of size which is pre-programmed by varying the length of the ISSAL supports. As is disclosed herein, varying the length of the ssDNA allows for larger or smaller liposome formulations. This size flexibility cannot be replicated using any other known design for liposome size adjustment. Normally liposomes are extruded through a filter and then frozen at a specific size, that size can be highly variable upon freeze-dry hydrodynamic reconstitution which curtails overall function mostly due the formation of multi-lamellar structures. Another example of this designs' superiority is in the ability to add membrane functionality in a step-wise manner to each liposome layer. This allows for membrane fusion events and affinity events to work in a concerted manner to break sub-cellular addresses. No other known liposome or virus design is capable of overcoming the issue of sub-cell addressing. Finally, the assembly of multiple layers of in the ISSAL allows for resistance to shape changes of the liposome during freeze-dry hydrodynamic reconstitution. Some liposome designs are capable of being highly resistant to hydrodynamic reconstitution, but at the expense of further functionality afforded by a fluid outer membrane. For example, a rigid outer encapsulating layer may allow for cell surface affinity by linking the encapsulating layer surface with antibodies, however there is no place for a membrane fusion protein to function due the restriction of the outer layer. The ISSAL design can allow for both hydrodynamic reconstitution as well as the addition of membrane fusion proteins along with any other desired membrane surface functionality.

The ISSAL's can be used in, for example and without limitation, the field of drug delivery, vaccination, imaging contrast agents, and nanotechnology, in which liposomes of ordered, self-assembling structure are employed to deliver soluble or insoluble molecules to any sub-cellular address. The self-assembling nature of this design also allows for a higher order assembly of larger structures based on a spherical starting point.

Examples

A 6-ended star DNA pattern was designed from 6 separate 33 base pair oligonucleotides with sequence symmetry minimization. Each oligonucleotide binds to its two neighbours with 9 base pairs each and has a terminal stretch of 15 base pairs of non-binding single stranded DNA. This 15 base pair stretch is identical between all oligonucleotides in the DNA pattern in order to act as acceptor ends for free pl-ssDNA. These oligonucleotides (Table 1), when placed in solution with a magnesium ion concentration of at least 5 mM form a three dimensional star shape with free single stranded 3' DNA ends. This star pattern is analogous to the "ISSAL core" described in center of Scheme 2. Three dimensional patterns were formed by mixing each oligonucleotide to a final concentration of 12 uM with 10 mM Mg2+ in 1× Tris/Boric acid/EDTA buffer with nuclease-free water. The DNA pattern oligonucleotides were heated to 95° C. for 10 minutes then decreasing sequentially from 65° C. to 45° C. to 35° C. to 25° C. for 20 minutes each. Pattern oligonucleotides were stored at −20° C. when not in use.

TABLE 1

DNA Sequences of an ISSAL Assembly

| Name | DNA Sequence 5' to 3' |
|---|---|
| 6 ended star pattern oligo 1 | CGTACGACGACCTCAACGCCACACCACTCCACC |
| 6 ended star pattern oligo 2 | CGTTGAGGTAGTGCAACGCCACACCACTCCACC |
| 6 ended star pattern oligo 3 | CGTTGCACTGGCACATCGCCACACCACTCCACC |
| 6 ended star pattern oligo 4 | CGATGTGCCGTGCGAACGCCACACCACTCCACC |
| 6 ended star pattern oligo 5 | CGTTCGCACCGACAGTCGCCACACCACTCCACC |
| 6 ended star pattern oligo 6 | CGACTGTCGCGTCGTACGCCACACCACTCCACC |
| 5'-Octadiynyl-complementary oligo | 5' Octadiynyl-dU-AGGTGGAGTGGTGTGG |

A phospholipid-ssDNA adduct molecule was synthesized by first joining an azide containing group to the head group of egg PE with N-hydroxysuccinimide (NHS) chemistry. The egg PE (0.1 g, Avanti Polar Lipids Inc.) was mixed with a slight molar excess of azido succinimidyl acetic acid NHS (0.03 g, Nanocs Inc.) in chloroform:methanol (10 mL, v/v=4:1) with triethylamine (0.15% v). The reaction was stirred overnight at room temperature under nitrogen. Deionized water (5 mL) was added to the reaction mixture and allowed to stir for 30 minutes to hydrolyze excess NHS reagent. The solvents were then evaporated with a rotary evaporator. The crude product was then resuspended in chloroform:methanol (10 mL, v/v=1:1) and placed into a 15 mL polypropylene tube. Water (1.25 mL) was added to the mixture for a final solution ratio of chloroform:methanol:water (11.25 mL, v/v/v=2:2:1). The mixture was shaken briefly and spun in a centrifuge at 3200×g for 8 minutes causing the chloroform and methanol:water layers to separate. The upper methanol:water layer was removed carefully and the lower chloroform layer placed in a pre-weighed glass vial. The vial was then placed in a vacuum oven overnight to evaporate the chloroform. The product weighed 0.1222 g for a percent yield of 110%. This product phosphatidylethanolamine-N-azidoacetamide (PE-azide) was analyzed by mass spectrometry to have an average molecular weight of 799.53 g/mol which corresponded to the addition of the azide group to the egg PE mixture. The purity was assessed by thin layer chromatography to be approximately 80% product and 20% PE.

A complementary pairing oligonucleotide (Table 1) was synthesized with a 5'-Octadiynyl containing group (IDT Inc). PE-azide (0.0031 g, in 250 uL chloroform) was mixed with the 5'-Octadiynyl-oligonucleotide (1 umol, 750 uL nuclease free water) for a molar equivalence of 4 PE-azide to 1 equivalent oligo. Separately, a mixture of copper(II) sulfate (1.24×10-5 g, 0.05 molar equivalent) and ascorbic acid (4.4×10-5 g, 0.25 molar equivalent) in water. The copper/ascorbic acid mixture (10 uL) was then added to the PE-azide/oligonucleotide mixture and the reaction was stirred vigorously overnight at room temperature. The product was then aliquoted into separate polypropylene tubes and placed in the vacuum oven overnight. The combined yield of the reaction was 0.0081 g or a percent yield of 95% as an example of a pl-ssDNA.

Liposomes were prepared by first creating a solution of pl-s sDNA in nuclease free water. 6-Ended DNA patterns in the appropriate buffer (x mol equivalence) were mixed with pl-ssDNA solution (20 to 400× mol equivalence) and phosphatidylcholine (dissolved in ethanol, 50 to 500× mol equivalence). Liposomes were prepared by heating the mixture to between 45 and 70° C. with medium intensity ultrasonication for 10-30 minutes. Table 2 shows an example of a mixing strategy for assembly of ISSAL liposomes. FIG. 1 shows electron micrograph images of prepared negative control and ISSAL liposomes (Table 2). FIG. 1 shows electron microscopy images of liposomes negative stained with uranyl acetate. Control samples with non-complimentary ISSAL "core" DNA patterns do not form organized structures at 10 nm (A and B). Properly formed ISSAL liposomes assemble at the expected size range (C and D).

Aggregation seen in C and D is likely due to excess DNA pattern oligos crosslinking individual liposomes into grape-like clusters. Images were taken at 200000× magnification using JEOL 1200 TEMSCAN microscope.

TABLE 2

Solution and mixing parameters for liposomes imaged by electron microscopy

| Name of Component and Mixing Order | Stock Concentration | Final Concentration | Volume (uL) |
|---|---|---|---|
| Tris Base/Boric Acid/EDTA Buffer | 5X solution | 1X | 8 |
| Magnesium Acetate | 100 mM | 10 mM | 4 |
| Nuclease Free Water | — | — | 10 |
| Fluorescent DNA Probe (binds to core pattern single stranded ends) | 10 uM | 1 uM | 4 |
| Assembled 6-Ended DNA Star Pattern (from Table 1) or control pattern with non-complementary ends | 12 uM | 1.2 uM | 4 |
| Samples were allowed to mix for 5 minutes at room temperature in order to anneal the fluorescent probe to the DNA star pattern | | | |
| PE-azide-oligo synthesized in [0064] | 1.6 mg/mL | 0.32 mg/mL | 8 |
| Samples were mixed and sonicated for 5 minutes at 68° C. using a Branson 2200 Ultrasonicating Water Bath. This step helps to break up PE-azide-oligo micelles for incorporation into ISSAL liposomes. | | | |
| Egg phosphatidylcholine in ethanol | 1.26 mg/mL | 0.063 mg/mL | 2 |
| Total Solution Volume | | | 40 |
| Samples were mixed again sonicated for 25 minutes at 68° C. And briefly centrifuged to collect solution. Samples placed at 4° C. overnight and imaged the next day | | | |

Other embodiments and uses of the invention will be apparent to those skilled in the art from consideration of the specification and practice of the invention disclosed herein. All patents, patent applications, and other references noted herein for whatever reason are specifically incorporated by reference. The specification and examples should be considered exemplary only with the true scope and spirit of the invention indicated by the following claims.

Certain adaptations and modifications of the described embodiments can be made. Therefore, the above discussed embodiments are considered to be illustrative and not restrictive.

1. Varma, M. V., Khandavilli, S., Ashokraj, Y., Jain, A., Dhanikula, A., Sood, A., Thomas, N. S., Pillai, O., Sharma, P., Gandhi, R. et al. 2004. Biopharmaceutic classification system: a scientific framework for pharmacokinetic optimization in drug research. *Curr. Drug Metab.* 5:375-388.

2. Shaw, J. P., Kent, K., Bird, J., Fishback, J., and Froehler, B. 1991. Modified deoxyoligonucleotides stable to exonuclease degradation in serum. *Nucleic Acids Res.* 19:747-750.
3. Xu, L., and Anchordoquy, T. 2011. Drug delivery trends in clinical trials and translational medicine: challenges and opportunities in the delivery of nucleic acid-based therapeutics. *J. Pharm. Sci.* 100:38-52.
4. Kringelum, J. V., Nielsen, M., Padkjaer, S. B., and Lund, O. 2012. Structural analysis of B-cell epitopes in antibody:protein complexes. *Mol. Immunol.* 53:24-34.
5. Kasper, C. K. 1991. Complications of hemophilia A treatment:factor VIII inhibitors. *Ann N Y Acad Sci.* 614: 97-105.
6. Tani, J., Faustine, and Sufian, J. T. 2011. Updates on current advances in gene therapy. *West Indian Med. J.* 60:188-194.
7. Grieger, J. C., and Samulski, R. J. 2012. Adeno-associated virus vectorology, manufacturing, and clinical applications. *Methods Enzymol.* 507:229-254.
8. Jacobs, F., and Wang, L. 2011. Adeno-associated viral vectors for correction of inborn errors of metabolism: progressing towards clinical application. *Curr. Pharm. Des.* 17:2500-2515.
9. Peer, D., and Margalit, R. 2000. Physicochemical evaluation of a stability-driven approach to drug entrapment in regular and in surface-modified liposomes. *Arch. Biochem. Biophys.* 383:185-190.
10. Peer, D., Karp, J. M., Hong, S., Farokhzad, O. C., Margalit, R., and Langer, R. 2007. Nanocarriers as an emerging platform for cancer therapy. *Nat. Nanotechnol* 2:751-760.
11. Guo, X., and Huang, L. 2012. Recent advances in nonviral vectors for gene delivery. *Acc. Chem. Res.* 45:971-979.
12. Cabrini, G., Bezzerri, V., Mancini, I., Nicolis, E., Dechecchi, M. C., Tamanini, A., Lampronti, I., Piccagli, L., Bianchi, N., Borgatti, M. et al. 2010. Targeting transcription factor activity as a strategy to inhibit pro-inflammatory genes involved in cystic fibrosis: decoy oligonucleotides and low-molecular weight compounds. *Curr. Med. Chem.* 17:4392-4404.
13. Top, D., de Antueno, R., Salsman, J., Corcoran, J., Mader, J., Hoskin, D., Touhami, A., Jericho, M. H., and Duncan, R. 2005. Liposome reconstitution of a minimal protein-mediated membrane fusion machine. *EMBO J.* 24:2980-2988.
14. Barry, C., Key, T., Haddad, R., and Duncan, R. 2010. Features of a spatially constrained cystine loop in the p10 FAST protein ectodomain define a new class of viral fusion peptides. *J. Biol. Chem.* 285:16424-16433.
15. Peer, D., Florentin, A., and Margalit, R. 2003. Hyaluronan is a key component in cryoprotection and formulation of targeted unilamellar liposomes. *Biochim. Biophys. Acta* 1612:76-82.
16. Rothemund, P. W. 2006. Folding DNA to create nanoscale shapes and patterns. *Nature* 440:297-302.
17. Dutse, S. W., and Yusof, N. A. 2011. Microfluidics-based lab-on-chip systems in DNA-based biosensing: an overview. *Sensors (Basel)* 11:5754-5768.
18. Walsh, A. S., Yin, H., Erben, C. M., Wood, M. J., and Turberfield, A. J. 2011. DNA cage delivery to mammalian cells. *ACS Nano* 5:5427-5432.
19. Sun, P., Tropea, J. E., and Waugh, D. S. 2011. Enhancing the solubility of recombinant proteins in *Escherichia coli* by using hexahistidine-tagged maltose-binding protein as a fusion partner. *Methods Mol. Biol.* 705:259-274.
20. Bumb, A., Brechbiel, M. W., Choyke, P. L., Fugger, L., Eggeman, A., Prabhakaran, D., Hutchinson, J., and Dobson, P. J. 2008. Synthesis and characterization of ultra-small superparamagnetic iron oxide nanoparticles thinly coated with silica. *Nanotechnology* 19:335601.
21. Ferrari, E., Darios, F., Zhang, F., Niranjan, D., Bailes, J., Soloviev, M., and Davletov, B. 2010. Binary polypeptide system for permanent and oriented protein immobilization. *J. Nanobiotechnology* 8:9.
22. Biswas, S., Dodwadkar, N. S., Sawant, R. R., and Torchilin, V. P. 2011. Development of the novel PEG-PE-based polymer for the reversible attachment of specific ligands to liposomes: synthesis and in vitro characterization. *Bioconjug. Chem.* 22:2005-2013.

What is claimed is:

1. An internal structured self assembled liposome (IS-SAL), comprising:
    a nuclear core molecule or complex comprising a first nucleic acid molecule; and
    a first lipid bilayer surrounding the nuclear core molecule or complex, the first lipid bilayer comprising a phospholipid coupled to a second nucleic acid molecule, wherein the second nucleic acid molecule extends from an internal surface of the first lipid bilayer and is complementary and coupled to the first nucleic acid molecule, wherein the nuclear core molecule or complex comprises:
        a micelle forming phospholipid coupled to the first nucleic acid molecule;
        a protein coupled to the first nucleic acid molecule; or
        a group of oligonucleotide forming a three dimensional pattern and having free unpaired oligonucleotide sequences.
2. The ISSAL of claim 1, wherein the first nucleic acid molecule is
    an oligonucleotide;
    a deoxyribonucleic acid (DNA) oligonucleotide; or
    a single stranded DNA (ssDNA).
3. The ISSAL of claim 2, wherein the ssDNA is coupled via the 5'-phosphate of the ssDNA.
4. The ISSAL of claim 1, wherein the phospholipid is phosphatidylethanolamine (PE).
5. The ISSAL of claim 1, wherein the second nucleic acid molecule is:
    an oligonucleotide, capable of coupling to the first nucleic acid molecule; or
    a single stranded deoxyribonucleic acid (ssDNA) oligonucleotide.
6. The ISSAL of claim 1, further comprising the second nucleic acid molecule extending from an external surface of the liposome.
7. The ISSAL of claim 6, further comprising a second lipid bilayer surrounding the first lipid bilayer, the second lipid bilayer comprising a second phospholipid coupled to a third nucleic acid molecule, wherein the third nucleic acid molecule extends from an internal surface of the second lipid bilayer and is coupled to the second nucleic acid molecule extending from the external surface of the first lipid bilayer.
8. The ISSAL of claim 1, further comprising an active pharmaceutical ingredient (API).
9. The ISSAL of claim 8, wherein the API is at least partly insoluble in an aqueous environment.
10. The ISSAL of claim 8, wherein the API is present in the lipid bilayer.
11. The ISSAL of claim 1, further comprising a membrane affinity or membrane fusion molecules.

12. The ISSAL of claim 11, wherein the membrane affinity or membrane fusion molecules comprises a surface antibody or a membrane fusion protein.

13. A method of forming the ISSAL as defined in claim 1, comprising the step of mixing the nuclear core molecule or complex with the phospholipid under conditions to effect formation of the ISSAL.

14. Use of the ISSAL as defined in claim 1, in the treatment of a disease.

15. A method of delivering an active pharmaceutical ingredient to a patient in need thereof, comprising providing the active pharmaceutical ingredient in the ISSAL as defined claim 1.

16. A method of treatment of a disease, comprising providing to a patient in need thereof, an active pharmaceutical ingredient in the ISSAL as defined in claim 1.

17. A pharmaceutical composition comprising the ISSAL as defined in claim 1, and a pharmaceutically acceptable excipient.

18. A kit, comprising:
the ISSAL as defined in claim 1; and
instructions for use.

* * * * *